United States Patent
Kishida et al.

(10) Patent No.: US 6,251,411 B1
(45) Date of Patent: *Jun. 26, 2001

(54) COMPOSITION FOR HYDROPHOBIC COSMETIC PRODUCTS

(75) Inventors: Shigeru Kishida, Storrs; William Kalriess, Tolland, both of CT (US); Takako Wright, Farmersville, TX (US); Masaru Kobayashi, Woodstock, CT (US); Mark LePage, Webster, MA (US); Isao Imai, Saitama (JP)

(73) Assignee: U.S. Cosmetics Corporation, Dayville, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/310,428

(22) Filed: May 12, 1999

Related U.S. Application Data

(63) Continuation-in-part of application No. 09/299,846, filed on Apr. 26, 1999, which is a continuation-in-part of application No. 08/658,461, filed on Jun. 5, 1996, now Pat. No. 5,897,868.

(51) Int. Cl.$^7$ .............................. A61K 7/00; A61K 7/035
(52) U.S. Cl. .............................. 424/401; 424/69; 514/844
(58) Field of Search ....................... 424/401, 69; 514/844

(56) References Cited

U.S. PATENT DOCUMENTS 5,897,868 * 4/1999 Kobayashi et al. .................. 424/401

* cited by examiner

Primary Examiner—Thurman K. Page
Assistant Examiner—Blessing Fubara
(74) Attorney, Agent, or Firm—Greenberg Traurig LLP

(57) ABSTRACT

A composition for cosmetic products and a method for making the cosmetic products, the composition comprises particles of pigments and/or extender pigments, water-soluble metal salt, and one or more hydrophobidizing agents selected from hydrogenated lecithin, and water-soluble alkali salt of fatty acids, acylamino acids, and acyl collagen with the water-soluble metal salt and the one or more hydrophobidizing agents being prevented from chemically interacting with one another in the presence of ambient moisture prior to placement of the composition into an aqueous slurry by encapsulation or by entrapment of one of such materials.

22 Claims, No Drawings

COMPOSITION FOR HYDROPHOBIC COSMETIC PRODUCTS

This is a continuation-in-part of U.S. Ser. No. 09/299,846, filed Apr. 26, 1999, which was in turn a continuation-in-part of U.S. Ser. No. 08/658,461 filed Jun. 5, 1996, and issued as U.S. Pat. No. 5,897,868 on Apr. 27, 1999.

FIELD OF THE INVENTION

The present invention relates to compositions used in preparing cosmetic products and to such cosmetic products made therewith and specifically to liquid and solid cosmetic products for external use and having the characteristics of being smooth, adhesive, spreadable, and long-lasting.

BACKGROUND OF THE INVENTION

Solid or solid-like, cake cosmetic products, such as make up preparations (e.g. face powder, powder foundation, eye shadow, mascara, rouge and the like) are conventionally produced by filling a cosmetic powder into a metal or plastic pan or case followed by molding the powder by a press. In particular, the conventional manufacturing process for preparing cosmetic products includes mixing pigments, and extender pigments and then atomizing them until the colors are well dispersed and uniform. Oily ingredients and auxiliary agents, such as anti-bacterial agents, are added to the pigments and extender pigments and mixed and are atomized to disperse the oily ingredients. The resulting mixture is then screened and further mixed until a uniform cosmetic powder is obtained. The cosmetic powder is filled into a pan or case and molded by a press.

This conventional process has several disadvantages:

i) Pigments and extender pigments have inherent strong hydrophilic properties; whereby, they will fade and/or discolor, when contacted by perspiration, unless they are specially treated.

ii) The percentage of out-of-specification product is unacceptably high due to the non-uniformity of surface-color and/or surface-hardness of the molded cosmetic product.

iii) Multi-color molding and complex shape molding are quite expensive because of the cost of the shaping-mold, which is typically machined from metal.

iv) High labor costs are incurred, arising from the manual labor needed for adjustment and maintenance of equipment and the supply of bulk powder.

v) The loss of cosmetic powder during the molding process is significant.

vi) The work environment is undesirable due to the exposure of the workers to powdery dusty pigments and extender pigments.

It has previously been proposed to use pigments that have been made hydrophobic to solve problem (i). For example, pigments or extender pigments and/or substrates which are surface-treated with silicone are strongly hydrophobic and can be used to prevent color fading and to improve the duration of use before reapplication. They can also be used for two-way cake (wet/dry application) cosmetics.

While the use of polysiloxanes ameliorates problem (i), the molding process becomes more complex and time consuming, and problems (ii), (iii), (iv), (v), and (vi) remain unsolved.

There have been some suggestions to solve problems (ii), (iii), (iv), (v), and (vi). For example, Japanese Patent 07-29904 and U.S. Pat. No. 4,967,810 suggest the use of a slurry in which pigments, extender pigments and/or substrates, and oily ingredients are dispersed in an organic solvent for injection into the pan or case by an injection machine. These proposals may reduce the severity of problems (ii), (iii), (iv), and (v), but problem (vi) remains unsolved. Further, the choice of usable oily ingredients is restricted depending on the kind or nature of the organic solvent used. For example, non-uniformity of the product is observed when an alcohol is used as the organic solvent with a silicone oil as the oily ingredient of the cosmetic product.

In parent patent application U.S. Ser. No. 08/658,461, now U.S. Pat. No. 5,897,868 ('868 patent), a simplified process is described, to decrease the labor intensity of the conventional processes, to improve the work environment, and to provide a smooth, adhesive, spreadable, and long-lasting cosmetic product.

The invention of the parent '868 patent was based upon the discovery that when the pigments or extender pigments and/or substrates are made hydrophobic in an aqueous environment with an agent having a lipophilic moiety, such as water-insoluble metal salts of fatty acids, acylamino acids, hydrogenated lecithin, acyl collagen and the like, and rinsed and dried but not completely dried, the pigments remain hydrophilic until full drying. In such state the oily materials are added and the mixture thus formed is kneaded to form an aqueous slurry, the oily materials are uniformly bound to the surface of the pigments and extender pigments and are not disassociated. The parent '868 patent thus provided an aqueous slurry for cosmetic products with good dispersal characteristics (without the need for any irritating surfactants for the purpose of dispersing pigments, as is normally required for acceptable dispersal), which comprised particles of pigments and/or extender pigments having a lipophilic moiety attached-to-the surface thereof. This was in contrast to the simple non-attached coating as disclosed in the various Miyoshi U.S. Pat. Nos. 4,606,914, 4,623,074 and 4,863,800, used with the same general materials but which do require the use of surfactants for effecting a dispersion in an aqueous slurry; and a cosmetically acceptable oily ingredient dispersed in a liquid suspending medium consisting essentially of water. Though effective in processing and use and with superior resultant products, transportation of the slurry described in parent '868 patent is costly, due to the weight of liquid suspending medium.

SUMMARY OF THE INVENTION

It is therefore an object of the present invention to provide a composition and a processing method which improves both the characteristics and economics of cosmetics made in accordance with the teachings of the parent '868 patent by including all the components required by the parent patent except the liquid suspending medium, whereby transportation cost of the composition for preparing cosmetic product is reduced while processing is still simplified, and without problems engendered by ambient moisture.

Generally the present invention provides a composition for cosmetic products, which comprises particles of pigments and/or extender pigments, water-soluble metal salt, and one or more hydrophobidizing agents. As in the parent application the hydrophobidizing agents include hydrogenated lecithin and water-soluble alkali salt of fatty acids, acylamino acids, and acyl collagen and combinations thereof. Means are further provided to prevent premature chemical interaction resulting from ambient moisture prior to the addition of a liquid suspending medium containing water.

When liquid suspending medium containing water is added to the composition, the pigments and/or extender pigments are made hydrophobic with hydrophobidizing agent having a lipophilic moiety attached to the surface.

DETAILED DESCRIPTION OF THE INVENTION

In accordance with the present invention, when liquid suspending medium containing water is added, pigments or extender pigments are made hydrophobic in an aqueous environment with an agent having a lipophilic moiety, such as a water-insoluble polyvalent metal salt of a fatty acid, an acylamino acid, hydrogenated lecithin, acyl collagen or like materials. In particular, the surface of the particles of the pigments and extender pigments carry lipophilic moieties (provided by the fatty acid etc.) linked to the surface of the particles by means of the polyvalent metal. Suitable polyvalent metals include alkaline earth metals, such as magnesium, and calcium, and other polyvalent metals, such as aluminum, titanium, zinc, zirconium and the like. This linking is more than just a coating as takes place in prior art materials such as disclosed in said Miyoshi patents, with resultant differences in dispersion properties as discussed above.

After the liquid suspending medium containing water is added and the mixture is kneaded, liquid suspending medium and an oily substance (if desirable but not required) are added until the resultant slurry reaches an appropriate viscosity. This slurry is then used for the preparation of cosmetic products. The slurry composition may be (but not necessarily) injected into the back of a container for the cosmetic product by an injection machine, while the injected material is vacuum dehydrated via a filter on the top surface of the container. Then the cosmetic product is dried at an appropriate temperature. Alternatively, the slurry composition can be used as is.

When liquid suspending medium containing water is added, the pigments or extender pigments will be made hydrophobic thus carry lipophilic groups on the surface thereof as a result of the treatment with the water-insoluble polyvalent metal salt of the fatty acid or other treating agent. The oily substances (if added) will bind to the lipophilic radicals on the pigments or extender pigments by displacing the water surrounding the treated pigments or extender pigments after the process of kneading (mixing).

The pigments or extender pigments are coated with lipophilic-moieties and surrounding oily substance (if added), and are stable and form fine micelles and become a slurry without the use of a surfactant. The pigments and extender pigments are originally hydrophilic and do not require large energy to be dispersed in the water containing slurry. After the surface treatment, the surface of each particle is coated with lipophilic-moieties and further covered by the surrounding oily substance (if added). Thus, the pigments and extender pigments will not agglomerate and will have excellent dispersibility for cosmetic use.

Using the composition of the invention for hydrophobic pigments or extender pigments as described previously, cosmetic products with very intense color tone and without color bleeding can be produced. Moreover, the cosmetic products of the present invention do not exhibit color fading or color bleeding and have excellent skin "feel", adhesiveness, and smoothness compared to cosmetics that use pigments or extender pigments surface-treated in a conventional manner.

The agents useful for imparting hydrophobic properties to the pigments and extender pigments have a lipophilic moiety, and include water-insoluble polyvalent metal salts of fatty acids, acylamino acids, hydrogenated lecithin, acyl collagen and the like. Suitable polyvalent metals include the alkaline earth metals, such as magnesium or calcium, and other metals, such as aluminum, titanium, zinc or zirconium. Surface treatment agents having suitable lipophilic moieties are described in U.S. Pat. Nos. 4,606,914, 4,623,074 and 4,863,800 and Japanese Patents 60-69011 and 61-73775. The pigments and extender pigments may be made hydrophobic by adding liquid suspending medium containing water to the composition of current invention containing the pigment and extender pigment particles, a water-soluble metal salt having a lipophilic moiety, and a water-soluble polyvalent metal salt, whereby the lipophilic moiety becomes linked to the particles by means of the polyvalent metal.

The amount of the surface-treating agent used in the present invention is dependent upon the particle size or specific surface area of the pigments or extender pigments being treated. Suitably, the amount of the surface-treating agent is from about 0.1 to about 20% by weight based on weight of the pigments or extender pigments, preferably from about 2 to about 5% by weight.

Suitable fatty acids providing the lipophilic moiety include lauric acid, myristic acid, palmitic acid, oleic acid, stearic acid, isostearic acid, behenic acid and the like. Water-soluble salts of such fatty acids may be formed with sodium, potassium, lithium, ammonium, or amine.

Suitable acylamino acids include N-acyl-L-glutamic acid, N-acyl-N-methylglycine, N-acyl-N-methyl-:β-alanine and the like. The acyl group may include a residue of lauric acid, myristic acid, palmitic acid, oleic acid, stearic acid, isostearic acid, and behenic acid. Water-soluble salts of such acylamino acids may be formed with sodium, potassium, lithium, ammonium, or amine.

Suitable hydrogenated lecithins include (1) hydrogenated natural lecithin obtained by extraction of lecithin from egg yolk, soy bean oil, corn oil, and rapeseed oil followed by hydrogenation; and (2) hydrogenated synthetic lecithin. The iodine value of the hydrogenated lecithin should preferably be less than 30. The term "lecithin" refers to the overall composition; therefore, the lecithin which can be used in the present invention does not have to be pure phosphatidyl choline, but may contain other phospholipids and neutral fats in addition to phosphatidyl choline.

Suitable acyl collagens include those obtained by acylation of an oligopeptide or peptide. Useful oligopeptides or peptides are obtained by partially hydrolyzing protein and/or collagen and have n=1–100. The acyl group may include a residue of lauric acid, myristic acid, palmitic acid, oleic acid, stearic acid, isostearic acid, and behenic acid. Water-soluble salts of such acyl collagens may be formed with sodium, potassium, lithium, ammonium, or amine.

The water-soluble salts having a lipophilic moiety used in the present invention are soluble at room temperature or in warm water. When liquid suspending medium containing water is added to the composition of current invention, the lipophilic moiety of one or more of these salts is adsorbed on the surface of the pigment and/or extender pigment particles. In order to complete the adsorption of the lipophilic moiety, a water soluble polyvalent metal salt, such as a water-soluble salt of Al, Mg, Ca, Zn, Zr, or Ti is added in sufficient amount to give a proportion of 1–2 equivalents of the polyvalent metal salt of the fatty acid, acylamino acid, hydrogenated lecithin, or acyl collagen and the like. Useful water-soluble, polyvalent metal salts include aluminum sulfate, aluminum chloride, aluminum nitrate, aluminum potassium sulfate, magnesium sulfate, magnesium chloride, magnesium nitrate, magnesium potassium sulfate, calcium chloride, calcium nitrate, calcium acetate, zinc sulfate, zinc chloride, zinc nitrate, zinc acetate, zirconium sulfate, zirconium chloride, titanium oxysulfate, and titanium chloride. The polyvalent metal salt reacts with the salt of the fatty acid, acylamino acid, hydrogenated lecithin, acyl collagen and the like to form a water-insoluble reaction product which becomes chemically bound onto the surface of the pigment and extender pigment particles.

In accordance with the present invention, the hydrophobidizing agents and/or water-soluble metal salts are prevented from pre-mature reaction such as by being encapsulated by materials commonly used for encapsulation in the cosmetic or pharmaceutical industries (for other purposes), such as albumen and gelatin. Alternatively, the salts may be entrapped by porous materials, such as alumina, silica, titanium dioxide, zirconium oxide, zinc oxide, acrylate, nylon, and other cosmetically acceptable materials to prevent the undesirable premature reaction between hydrophobidizing agent and water-soluble metal salt that may be triggered by moisture during storage.

The oily substance used in the present invention may be any cosmetically acceptable oily substance commonly used in cosmetics. Examples of the oily substance include:

a) Silicone fluids: Methicone; Dimethicone; Cyclomethicone; Phenyl Methicone (Methylphenyl Polysiloxane); and other cosmetically acceptable silicone fluids;

b) Hydrocarbons: Mineral oil; Petrolatum; Isobutane; Isododecane; Isoeicosane; Isohexadecane; Isopentane; Paraffin; Squalane; Squalene; and other cosmetically acceptable hydrocarbons;

c) Vegetable and animal oils: Lanolin oil; Sunflower oil; Caster oil; Olive oil; Wheat germ oil; and other cosmetically acceptable vegetable and animal oils;

d) Fatty acids: isostearic acid; myristic acid; stearic acid; and other cosmetically acceptable fatty acids;

e) Esters: Mono-, di-, triglycerides; Octyldodecyl myristate; octyldodecyl oleate; octyldodecyl erucate; octyldodecyl ricinoleate; octyldodecyl laurate; octyldodecyl palmitate; octyldodecyl stearate; octyldodecyl isostearate; Hexyldecyl myristate; hexyldecyl laurate; hexyldecyl palmitate; hexyldecyl stearate; hexyldecyl isostearate; Neopentyl glycol dicaprate; neopentyl glycol diheptanoate; neopentyl glycol diisostearate; neopentyl glycol dilaurate; neopentyl glycol dioctanoate; Trioctanoin; isononyl isononanoate; and other cosmetically acceptable esters;

f) Ethers: Ethylene glycol; propylene glycol; butylene glycol; Polyethylene glycol; polypropylene glycol; and other cosmetically acceptable ethers;

g) Polyols: Glycerin

These oily substance may be one oily substance or a mixture thereof. The oily substance may be added to the pigments or extender pigments either before or after liquid suspending medium is added. The amount of the oily substance useful in the present invention is dependent upon the size, specific surface area, or oil absorption of the pigments or extender pigments being treated. Suitably, the amount of the oily material is from 0 to about 300% by weight of the pigments or extender pigments, preferably from about 2 to about 100% by weight.

The liquid suspending medium consisting essentially of water required for the reaction between hydrophobizing agent and water-soluble metal salt is not less than 10%, and is preferably from 10% to 450%, by weight with respect to the weight of pigment being dispersed.

The pigments or extender pigments used in the present invention include organic and inorganic pigments, such as titanium dioxide, zinc oxide, zirconium dioxide, yellow iron oxides, black iron oxides, red iron oxides, ultramarine blues, Prussian blues, chromium oxides, chromic hydroxides, and the like, pearlescent pigments, such as mica coated with titanium dioxide, bismuth oxychloride, coal-tar pigments, natural pigments, silica beads, nylon beads, acrylic beads, talc, kaolin, mica, mica-like minerals, such as sericite type materials, magnesium carbonate, calcium carbonate, aluminum silicate, magnesium silicate, calcium silicate and clay and the like.

The most distinctive feature of the present invention is the excellent dispersibility of fine particles or ultra fine pigment or extender pigment particles (those smaller than 1 micron), such as titanium dioxide, zinc oxide, yellow iron oxides, black iron oxides, red iron oxides, ultramarine blues, Prussian blues, chromium oxides, chromium hydroxides or coal tar pigments.

In addition to containing pigments and extender pigments as described above, molding additives may be included depending on the need, to further improve the product quality. These molding additives may be natural cellulose powder, metal soaps, calcium phosphates and like materials used in molding cosmetics or pharmaceuticals. If desired, humectants, binders and/or thickeners may also be used.

The invention is illustrated by means of preferred embodiments in the following examples.

EXAMPLE 1

PRESSED MAKE-UP-PRIOR ART

The following composition of pigments and extender pigments was mixed using a home type mixer and pulverized with a pulverizer:

| | |
|---|---|
| Talc | 43.7 g |
| Mica | 30.0 g |
| Dimethicone | 8.0 g |
| Titanium dioxide | 7.5 g |
| Yellow iron oxide | 2.5 g |
| Red iron oxide | 1.5 g |
| Black iron oxide | 0.3 g |
| Sodium palmitate | 3.5 g |
| Aluminum potassium sulfate | 3.0 g |

To above mixture, 200 g of water at 40° C. was added and mixed until well dispersed. The resultant slurry was injected into the rear of a pan using the injection machine described in U.S. Pat. No. 4,967,810, while excess water needed to make a finished pressed make-up was vacuum extracted from the product from the top of the surface via a filter. The cosmetic product was dried for 8 hours at room temperature. The pressed make-up product obtained had excellent hydrophobicity, skin feel, skin adhesion, extendibility, payoff and uniformity.

EXAMPLE 2

PRESSED MAKE-UP

The following composition of pigments and extender pigments was pulverized.

| | |
|---|---|
| Talc | 46.2 g |
| Mica | 30.0 g |
| Dimethicone | 8.0 g |
| Titanium dioxide | 7.5 g |
| Yellow iron oxide | 2.5 g |
| Red iron oxide | 1.5 g |
| Black iron oxide | 0.3 g |
| Potassium oleate | 3.0 g |
| (potassium oleate encapsulated in gelatin at 70:30 by weight) | |
| Aluminum chloride | 1.0 g |

To above mixture 150 g of water was added and mixed until well dispersed. The resultant slurry was injected into the rear of a pan using the injection machine described in U.S. Pat. No. 4,967,810, while excess water needed to make a finished pressed make-up was vacuum extracted from the product from the top of the surface via a filter. The cosmetic product was dried for 4 hours at 50° C. The pressed make-up product obtained had excellent hydrophobicity, skin feel, skin adhesion, extendibility, payoff and uniformity.

EXAMPLE 3

PRESSED MAKE-UP

The following composition of pigments and extender pigments was mixed using a home type mixer and pulverized with a pulverizer:

| | |
|---|---|
| Talc | 46.7 g |
| Mica | 30.0 g |
| Dimethicone | 8.0 g |
| Titanium dioxide | 7.5 g |
| Yellow iron oxide | 2.5 g |
| Red iron oxide | 1.5 g |
| Black iron oxide | 0.3 g |
| Hydrogenated lecithin | 1.5 g |
| Aluminum chloride | 2.0 g |
| (aluminum chloride entrapped in porous nylon 6 at 10:90 by weight) | |

To above mixture, 180 g of water at 75° C. was added and mixed until well dispersed. The resultant slurry was injected into the rear of a pan using the injection machine described in U.S. Pat. No. 4,967,810, while excess water needed to make a finished pressed make-up was vacuum extracted from the product from the top of the surface via a filter. The cosmetic product was dried for 6 hours at 40° C. The pressed make-up product obtained had exceptional skin feel, excellent hydrophobicity, skin adhesion, extendibility, payoff and uniformity.

It is evident from the above that treated pigments maintained in accordance with the present invention prior to mixing into a slurry provide cosmetic products on a par with similar materials initially processed in a slurry.

It is understood that the above description is exemplary of the present invention and that changes in components and relative amounts as well as processing steps are possible without departing from the scope of the present invention as defined in the following claims.

What is claimed is:

1. A composition for cosmetic products, which comprises particles of pigments and/or extender pigments, water-soluble metal salt, and one or more hydrophobidizing agents selected from hydrogenated lecithin, and water-soluble alkali salt of fatty acids, acylamino acids, and acyl collagen wherein said composition comprises means for substantially preventing the water-soluble metal salt and the one or more hydrophobidizing agents from chemically interacting with one another in the presence of ambient moisture prior to placement of the composition into an aqueous slurry.

2. The composition according to claim 1, wherein said water-soluble metal salt is a salt of a polyvalent metal.

3. The composition according to claim 2, wherein said polyvalent metal salt is a magnesium, calcium, aluminum, titanium, zinc or zirconium salt.

4. The composition according to claim 1, wherein said water-soluble alkali salt is a sodium, potassium, lithium, ammonium, and amine salt.

5. The composition according to claim 1, wherein said water-soluble alkali salt and hydrophobidizing agent are separated from each other in said composition by encapsulation by at least one of the water-soluble salt and hydrophobidizing agent with an encapsulation material.

6. The composition of claim 1, wherein the water-soluble alkali salt and hydrophobidizing agent are separated by means of entrapment of at least one of the water-soluble salt and hydrophobidizing agent in an entrapment material.

7. The composition according to claim 1, wherein said hydrophobidizing agents are from about 0.1% to about 20% based on the weight of the pigment and extender pigment particles.

8. A cosmetic product formed from the composition of claim 1.

9. A cosmetic product formed from the composition of claim 5.

10. A cosmetic product formed from the composition of claim 6.

11. A method for making the cosmetic product of claim 8, comprising the steps of:

a) dispersing the composition into a liquid suspending medium, b) adhering a lipophilic moiety to the surface of said particles while said particles are in said dispersion, and c) admixing a cosmetically acceptable additional component with said dispersion to form a slurry.

12. A method for making the cosmetic product of claim 9, comprising the steps of:

a) dispersing the composition into a liquid suspending medium, b) adhering a lipophilic moiety to the surface of said particles while said particles are in said dispersion, and c) admixing a cosmetically acceptable additional component with said dispersion to form a slurry.

13. A method for making the cosmetic product of claim 10, comprising the steps of:

a) dispersing the composition into a liquid suspending medium, b) adhering a lipophilic moiety to the surface of said particles while said particles are in said dispersion, and c) admixing a cosmetically acceptable additional component with said dispersion to form a slurry.

14. The cosmetic product of claim 8, wherein the liquid suspending medium consists essentially of water, and optionally a cosmetically acceptable oily substance.

15. The cosmetic product of claim 9, wherein the liquid suspending medium consists essentially of water, and optionally a cosmetically acceptable oily substance.

16. The cosmetic product of claim 10, wherein the liquid suspending medium consists essentially of water, and optionally a cosmetically acceptable oily substance.

17. A cosmetic product formed by drying the slurry of claim 11.

18. A cosmetic product formed by drying the slurry of claim 12.

19. A cosmetic product formed by drying the slurry of claim 13.

20. The cosmetic product formed by injecting the slurry of claim 11 through a back injection machine, dehydrated and dried.

21. The cosmetic product formed by injecting the slurry of claim 12 through a back injection machine, dehydrated and dried.

22. The cosmetic product formed by injecting the slurry of claim 13 through a back injection machine, dehydrated and dried.

* * * * *